(12) United States Patent
Matsunaga

(10) Patent No.: US 6,878,169 B2
(45) Date of Patent: Apr. 12, 2005

(54) HAIR DYE COMPOSITION

(75) Inventor: Kenichi Matsunaga, Darmstadt (DE)

(73) Assignee: Kao Corporation, Tokyo (JP)

( * ) Notice: Subject to any disclaimer, the term of this patent is extended or adjusted under 35 U.S.C. 154(b) by 104 days.

(21) Appl. No.: 10/319,589

(22) Filed: Dec. 16, 2002

(65) Prior Publication Data

US 2003/0188390 A1 Oct. 9, 2003

(30) Foreign Application Priority Data

Apr. 8, 2002 (EP) .............................. 02007368

(51) Int. Cl.$^7$ .............................. A61K 7/13
(52) U.S. Cl. ............... 8/405; 8/407; 8/426; 8/441; 8/454; 8/462; 8/463; 8/568; 8/570; 8/572; 8/573; 8/574; 132/208; 458/455
(58) Field of Search .................. 8/405, 407, 426, 8/441, 454, 462, 463, 568, 570, 572, 573, 574; 132/208; 458/455

(56) References Cited

U.S. PATENT DOCUMENTS

| | | | |
|---|---|---|---|
| 4,542,224 A | * | 9/1985 | Raue et al. ........... 548/455 |
| 4,605,441 A | | 8/1986 | Masuda et al. .......... 66/21 |
| 5,593,459 A | | 1/1997 | Gamblin et al. .......... 8/539 |
| 5,879,412 A | * | 3/1999 | Rondeau et al. .......... 8/411 |
| 6,451,069 B1 | | 9/2002 | Matsunaga et al. ........ 8/405 |
| 6,547,834 B1 | | 4/2003 | Matsunaga et al. ........ 8/405 |
| 6,592,630 B1 | | 7/2003 | Matsunaga et al. ........ 8/405 |

FOREIGN PATENT DOCUMENTS

| | | |
|---|---|---|
| JP | 58-002204 | 1/1983 |
| JP | 6-271435 | 9/1994 |
| JP | 08-501322 | 2/1996 |
| JP | 08-507545 | 8/1996 |
| JP | 09-118832 | 5/1997 |
| JP | 6-271435 | 9/2004 |
| WO | WO 99/07334 | 2/1999 |
| WO | WO 01/78670 | 10/2001 |
| WO | WO 01/78671 | 10/2001 |

OTHER PUBLICATIONS

Patent Abstracts of Japan, JP 63–129352, Jun. 1, 1988.
Patent Abstracts of Japan, JP 06–336086, Dec. 6, 1994.
Patent Abstracts of Japan, JP 07–061142, Mar. 7, 1995.
Dokl. Akad. Nauk SSSR (1968), 179(3), 596–9.
E.B. Lifshits, "Solvatochromism of Cyanine Dyes", Doklady Chemistry, Proceedings of the Academy of Sciences of the USSR, vol. 179, Nos. 1–3, Mar. 1968, pp. 258–260.

* cited by examiner

Primary Examiner—Margaret Einsmann
Assistant Examiner—Eisa Elhilo
(74) Attorney, Agent, or Firm—Oblon, Spivak, McClelland, Maier & Neustadt, P.C.

(57) ABSTRACT

Provided is a hair dye composition containing a direct dye (1):

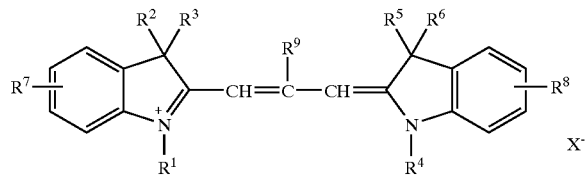

[wherein, $R^1$, $R^2$, $R^3$, $R^4$, $R^5$ and $R^6$ each represents a $C_{1-6}$ alkyl group; $R^7$ and $R^8$ each represents a hydroxy group, a $C_{1-6}$ alkyl group, a $C_{1-6}$ alkoxy group, an amino group or alkylamino groups; $R^9$ represents a hydrogen atom or a $C_{1-6}$ alkyl group; and $X^-$ represents an anion].

This hair dye composition undergoes a small change in color tone even after storage because it contains the direct dye (1) which has high stability against any one of an alkali agent, oxidizing agent and reducing agent, and at the same time, has markedly high hair dyeing power and exhibits excellent light resistance, washing resistance, perspiration resistance, friction resistance and heat resistance.

21 Claims, No Drawings

HAIR DYE COMPOSITION

TECHNICAL FIELD

The present invention relates to a hair dye composition that provides high dyeing power, can strongly impart the hair with an extremely vivid color within a color range of purple to blue, has less color fade over time and undergoes only a small change in the color tone even after storage.

BACKGROUND ART

Hair dyes can be classified by the dyes to be used or by whether they have any bleaching action on melanin. Typical examples include a two-part permanent hair dye composed of a first part containing an alkali agent, an oxidation dye and optionally a direct dye such as a nitro dye and a second part containing an oxidizing agent; and a one-part semi-permanent hair dye containing an organic acid or an alkali agent, and a direct dye such as acid dye, basic dye or nitro dye.

The above-described permanent hair dye is however accompanied with the drawbacks that the color tone imparted by an oxidation dye is not so vivid and that the color of the hair dyed with a vivid-color producing nitro dye ordinarily employed as a direct dye markedly fades over time and becomes dull quickly even if the color tone immediately after dyeing is very vivid (Japanese Laid-Open Publication No. Hei 6-271435).

Recently, hair dyes containing a so-called cationic dye have been reported. The cationic dye however involves the drawback that it is unstable against an alkali agent used for an alkali semi-permanent or permanent hair dye, hydrogen peroxide used as an oxidizing agent for a two-part hair dye or a reducing agent added to a permanent hair dye. In the pamphlet of International Patent Application Laid-Open No. 99/07334 (which will hereinafter be called "WO99/07334"), described is a hair dye containing a specific methine type cationic dye stable against an oxidizing agent, a reducing agent or the like. According to the investigation by the present inventor, however, any one of the methine type cationic dyes disclosed specifically in the pamphlet had insufficient stability upon storage within a pH range of 2 to 11, that is, a pH range ordinarily employed for a hair dye. Described specifically, these methine type cationic dyes were particularly unstable against an alkali agent. In a hair dye containing an alkali agent, they decomposed with the passage of time after storage and lost most or their dyeing property. Even when the hair dye was used within an acid to neutral pH range, they gradually decomposed and their dyeing property lowered. In addition, it has been revealed that mixing with a second component part containing an oxidizing agent causes prompt decomposition of them, thereby lowering their dyeing property and in a permanent hair dye containing a reducing agent, their dyeing property is impaired by the storage, thus showing that their stability against an oxidizing agent and a reducing agent is considerably insufficient contrary to the description in the pamphlet.

DISCLOSURE OF THE INVENTION

An object of the present invention is to provide a hair dye composition which shows high storage stability within a pH range of from 2 to 11 which is a pH range ordinarily employed for a hair dye, is stable against any one of an alkali agent, an oxidizing agent and a reducing agent, has high hair dyeing power, has less color fade over time, and undergoes only a small change in dyeing property or color tone even by storage.

The present inventor has found that a methine type cationic dye having a specific structure which is embraced in the scope of the formula described in the claim of WO99/07334 but not disclosed specifically, have markedly higher storage stability, particularly, high storage stability against any one of an alkali agent, an oxidizing agent and a reducing agent, compared with the other methine type cationic dyes disclosed specifically in the pamphlet. The present inventor has also found that a hair dye composition containing this dye can strongly impart the hair with an extremely vivid color within a color range of purple to blue (whereas Basic Red 12 disclosed in previous patent can impart the hair with only a vivid red color) and has excellent light resistance, washing resistance, perspiration resistance, friction resistance and heat resistance, and undergoes only a very small change in the color tone after storage compared with that immediately after preparation.

In one aspect of the present invention, there is thus provided a hair dye composition comprising, as a direct dye, a compound represented by the following formula (1):

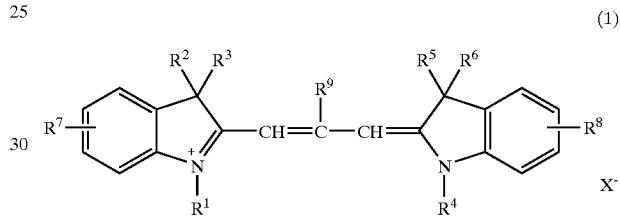

[wherein, $R^1$, $R^2$, $R^3$, $R^4$, $R^5$ and $R^6$ each independently represents a $C_{1-6}$ alkyl group which may have a substituent; $R^7$ and $R^8$ each independently represents a hydroxy group, a $C_{1-6}$ alkyl group which may be substituted by a hydroxy group, a $C_{1-6}$ alkoxy group, an amino group which may be substituted with one or two $C_{1-6}$ alkyl groups which may be substituted by a hydroxy group; $R^9$ represents a hydrogen atom or a $C_{1-6}$ alkyl group; and $X^-$ represents an anion].

In another aspect of the present invention, there is also provided a hair dyeing method comprising applying the above-described hair dye composition to the hair.

BEST MODE FOR CARRYING OUT THE INVENTION

In the formula (1), examples of the $C_{1-6}$ alkyl group represented by $R^1$, $R^2$, $R^3$, $R^4$, $R^5$ or $R^6$ include methyl, ethyl, propyl, butyl, pentyl, hexyl, isopropyl, isobutyl and isopentyl groups. $R^1$, $R^2$, $R^3$, $R^4$, $R^5$ and $R^6$ may be the same or different. Examples of the substituent which $R^1$, $R^2$, $R^3$, $R^4$, $R^5$ or $R^6$ may have include sulfonic acid group or salts thereof, cyano group, chlorine atom, hydroxy group, amino group, alkoxy groups, monoalkylamino groups, dialkylamino groups, trimethylammoniumyl group and aryl groups. As $R^1$ to $R^6$, a methyl group is most preferred from the viewpoints of production ease of a dye and availability of raw materials for production.

As $R^7$ or $R^8$, examples of the $C_{1-6}$ alkyl group which may be substituted by a hydroxy group include, in addition to the above-exemplified $C_{1-6}$ alkyl groups, hydroxymethyl group, 1-hydroxyethyl group, 2-hydroxyehtyl group, 1-hydroxypropyl group and 3-hydroxypropyl groups. Examples of the $C_{1-6}$ alkoxy group represented by $R^7$ or $R^8$ include methoxy, ethoxy, propoxy, butoxy, pentyloxy, hexyloxy, isopropoxy, isobutoxy and isopentyloxy groups. Examples of the amino group which may be substituted with one or two $C_{1-6}$ alkyl groups which may be substituted by a hydroxy group include amino, monomethylamino, dimethylamino, monoethylamino, diethylamino, monopropylamino, dipropylamino, mono(2-hydroxyethyl) amino, bis(2-hydroxyethyl)amino, mono(2-hydroxypropyl) amino, bis(2-hydroxypropyl)amino, mono(3-hydroxypropyl)amino, bis(3-hydroxypropyl)amino groups.

As $R^7$ and $R^8$, a hydroxy group, methoxy group, amino group or dimethylamino group is more preferred from the viewpoints of production ease of a dye and availability of raw materials for production. As $R^9$, the above-exemplified alkyl groups are preferred for stability of the resulting dye because use of them tends to improve the stability. Since the dye has sufficient stability when a hydrogen atom is used as $R^9$, however, a hydrogen atom is most preferred from the viewpoints of production ease of the dye and availability of raw materials for production.

In the formula (1), examples of the anion represented by $X^-$ include chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions, acetic acid ions and perchloric acid ions.

As the preferred structure of the direct dye (1) is represented by the following formula (2)

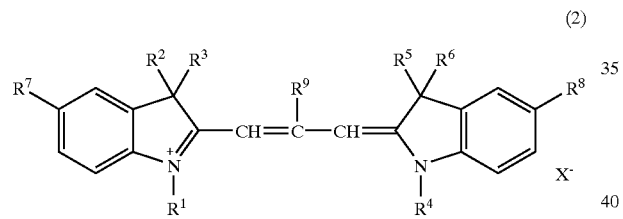

(2)

[wherein each of $R^1$, $R^2$, $R^3$, $R^4$, $R^5$, $R^6$, $R^7$, $R^8$, $R^9$ and $X^-$ has the same meanings as described above]

As the preferred specific examples of the direct dye (1), dye-(a), dye-(b) and dye-(c), which are represented by the below-described formulas can be mentioned in the literature titled "Solvatochromism of cyanine dye" (Dokl. Akad. Nauk SSSR (1968), 179(3), 596–9.)

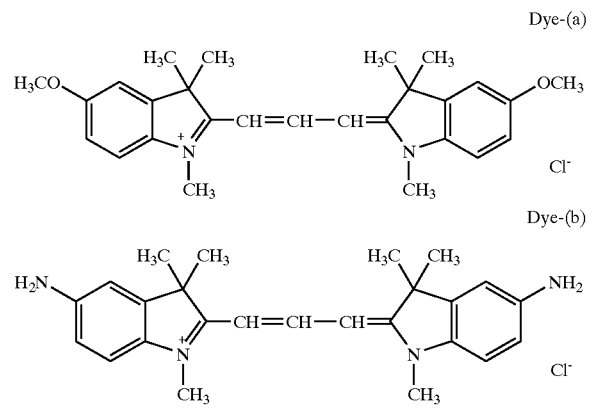

Dye-(a)

Dye-(b)

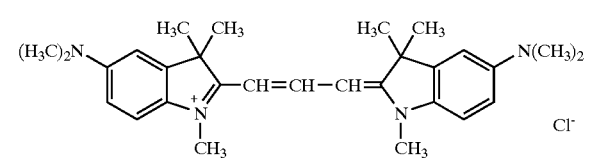

Dye-(c)

As the direct dye (1), one or more can be used. Alternatively it may be used in combination with another direct dye. In particular, combination of the direct dye (1) with yellow and red dyes makes it possible to dye the hair with a deep and highly lustrous dark brown or black color.

Examples of the direct dye other than the direct dyes (1) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 46 (C.I. 110825), Basic Red 76 (C.I. 12245), Basic Red 118 (C.I. 12251:1), Basic Yellow 28 (C.I. 48054) and Basic Yellow 57 (C.I. 12719); cationic dyes as described in Japanese Patent Publication No. Sho 58-2204, Japanese Patent Application Laid-Open (kokai) No. Hei 9-118832, Japanese Language Laid-Open Publications (PCT) Nos. Hei 8-501322 and Hei 8-507545; and methine type cationic dyes having a cyanine structure represented by the below-described formulas.

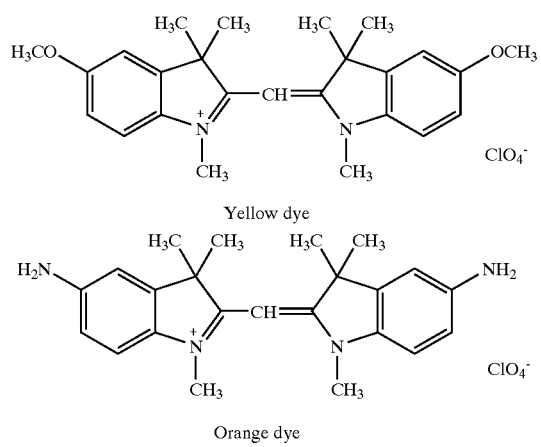

Yellow dye

Orange dye

The direct dye (1) is preferably added in an amount of 0.01 to 20 wt. %, more preferably 0.05 to 10 wt. %, especially 0.1 to 5 wt. % based on the whole composition (after mixing of all the component parts when the composition is a two part or three part composition; this will be applied equally hereinafter). When another direct dye is used in combination, the content of it in total with the direct dye (1) preferably ranges from 0.05 to 10 wt. %, especially 0.1 to 5 wt. %.

In the hair dye composition of the present invention, the direct dye (1) exhibits high storage stability within a wide pH range from 2 to 11 which is a pH range employed ordinarily for hair dyes, so that the hair dye composition can be used freely in the above-described pH range. Use in a pH range of 5 or greater is however preferred from the viewpoint of dyeing property. Moreover, owing to high stability of the direct dye against an alkali agent, the hair dye composition can be used at a pH not less than 8, particularly 8 to 11 which permits high dyeing power and even after storage for a long period of time, it exhibits high dyeing power without decomposition of the direct dye. Examples of the alkali agent include ammonia, alkanolamines such as monoethanolamine and isopropanolamine or salts thereof, guanidium salts such as guanidine carbonate and hydroxide salts such as sodium hydroxide. The alkali agent is preferably added in an amount of 0.01 to 20 wt. %, more preferably 0.1 to 10 wt. %, especially 0.5 to 5 wt. % based on the whole composition.

Since in the hair dye composition of the present invention, the direct dye (1) has high stability against an oxidizing agent, it can be applied to the hair after mixing with an oxidizing agent. In other words, it can be provided in the form composed of a first component part containing the direct dye (1) and a second component part containing an oxidizing agent. In this case, hair dyeing and bleaching can be carried out simultaneously, which facilitates more vivid hair dyeing. Examples of the oxidizing agent include hydrogen peroxide, persulfates such as ammonium persulfate, potassium persulfate and sodium persulfate, perborates such as sodium perborate, percarbonates such as sodium percarbonate and bromates such as sodium bromate and potassium bromate. Hydrogen peroxide is especially preferred for hair bleaching property, stability of the dye and availability. The oxidizing agent is preferably added in an amount of 0.5 to 10 wt. %, especially 1 to 8 wt. %, based on the whole composition. The mixing ratio of the first component part containing the direct dye (1) with the oxidizing-agent-containing second component part preferably ranges from 2:1 to 1:3 in terms of a volumetric ratio.

In the hair dye composition of the present invention, the direct dye (1) has high stability against a reducing agent to be used for improving the storage stability of an oxidation dye, which makes it possible to use it in combination with an oxidation dye. The combined use attains a markedly more vivid and stronger color which is not possible by the use of an oxidation dye alone.

Examples of the reducing agent include sulfites, thioglycolic acid and ascorbic acid. It is preferably added in an amount of 0.1 to 5 wt. %, especially 0.3 to 3 wt. % in the whole composition. As the oxidizing agent, the above-exemplified ones are usable, with hydrogen peroxide being particularly preferred.

For the oxidation dye, known developers and couplers ordinarily employed for an oxidation type hair dye can be used.

Examples of the developer include paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethylpara-phenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraaminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine and 4,5-diamino-1-(4'-chlorobenzyl)pyrazole and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylaminotoluene, 2,4-diamino-5-fluorotoluene, 1,3-bis(2,4-diaminophenoxy)propane, metaaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

At least one of the above-exemplified ones can be used as the developer and coupler. The level of each of the developer and coupler is preferably 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant, anionic polymer or fatty acid) is added to the hair dye composition of the present invention, the following equation is preferably satisfied:

"Ion activity concentration of the anionic component/Ion activity concentration of the direct dye (1)$\leq 8$"

The term "ion activity concentration" as used herein means "molar concentration×ionic valence".

Addition of a polyol, polyol alkyl ether, cationic or amphoteric polymer or silicone to the hair dye composition of the present invention is preferred, because the resulting composition can dye the hair uniformly and has improved cosmetic effects of the hair.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first component part containing an alkali agent and a second component part containing an oxidizing agent, or a three-part composition having, in addition to these two component parts, a powdery oxidizing agent such as persulfate. The direct dye (1) may be incorporated in either one or both of these component parts of the two-part or three-part composition. When the hair dye composition of the present invention is one-part type, it is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mPa·s in the stage of application to the hair (after mixing of all the component parts when the composition is a two-part or three-part type)

EXAMPLES

Dyes employed in Examples and Comparative Examples are shown below.

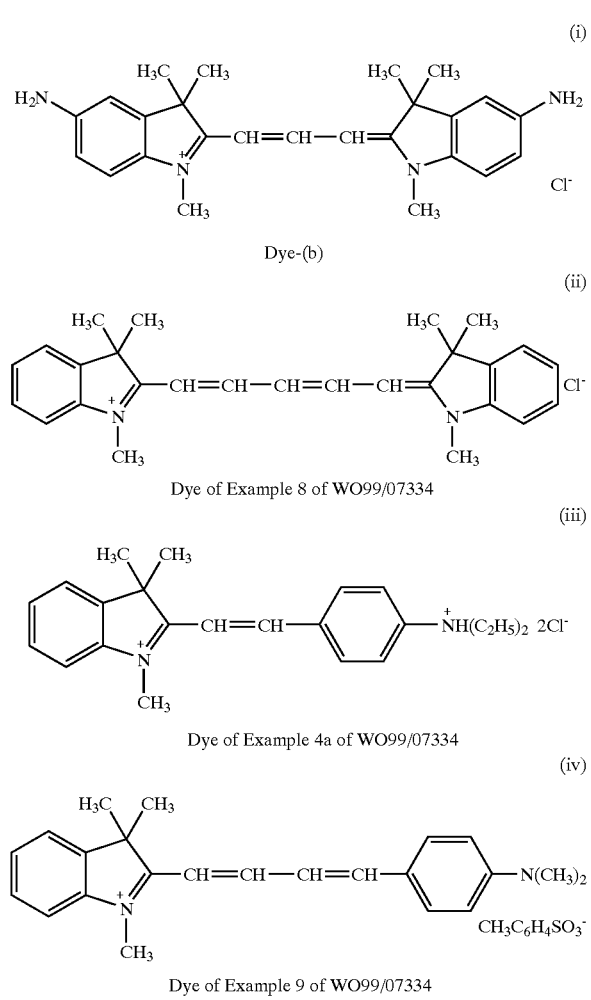

Dye-(b) (i)

Dye of Example 8 of WO99/07334 (ii)

Dye of Example 4a of WO99/07334 (iii)

Dye of Example 9 of WO99/07334 (iv)

Example 1 and Comparative Examples 1 to 3

A two-part hair dye as described below was prepared and its stability against each of an oxidizing agent and an alkali agent was evaluated. It should be noted that in each of the hair dyes, the pH of the first component part was 9.5, that of the second component part was 4.3 and that of a mixture thereof was 9.3.

| | (wt. %) |
|---|---|
| (First component part) | |
| 25 wt. % Aqueous ammonia | 6.0 |
| Ammonium chloride | 2.7 |
| Ethanol | 10.0 |
| Propylene glycol | 10.0 |
| The dye shown in Table 1 | 0.1 |
| Deionized water | balance |
| (Second component part) | |
| 35 wt. % Aqueous hydrogen peroxide | 17.1 |
| Deionized water | balance |

(Evaluation Method)

A 1:1 mixture (weight ratio) of the first component part and second component part was used as a test solution. The test solution (10 g) and a bundle of the goat's hair (10 cm in length and 1 g in weight) were charged in a test tube. It was allowed to stand for 20 minutes in a thermostat of 30° C. The hair bundle was then rinsed with warm water, washed twice with a shampoo and then dried. The color of the hair bundle thus dyed was evaluated based on the below-described standards.

(Evaluation Standards)

A: The hair can be dyed excellently and uniformly.
B: The hair can be dyed well and uniformly.
C: The hair cannot be dyed well.
D: The hair can hardly be dyed.

(Results)

As is apparent from the results shown in Table 1, Dye (i) has higher stability against an oxidizing agent and an alkali agent and is markedly superior in dyeing property of the hair compared with the typical methine dyes (ii) to (iv) disclosed in WO99/07334.

TABLE 1

| | Direct dye | Evaluation of dyeing property | Remarks |
|---|---|---|---|
| Example 1 | Dye (i) | A | — |
| Comp. Ex. 1 | Dye (ii) | C | Lightening of the color |
| Comp. Ex. 2 | Dye (iii) | D | (decomposition of dye) of the dye |
| Comp. Ex. 3 | Dye (iv) | D | solution was observed during dyeing |

Example 2 and Comparative Examples 4 to 6

The one-part hair dye (pH 9.5) as shown below was prepared and its storage stability against an alkali agent was evaluated.

| | (wt. %) |
|---|---|
| 25 wt. % Aqueous ammonia | 6.0 |
| Ammonium chloride | 2.7 |
| Ethanol | 10.0 |
| Propylene glycol | 10.0 |
| The dye shown in Table 2 | 0.1 |
| Deionized water | Balance |

(Evaluation Method)

In a similar manner and in accordance with similar standards to Example 1 except for the use of 10 g of each of the above-described one-part hair dye just after preparation and the hair dye 3 months after storage at 40° C., the dyeing property was evaluated.

(Results)

As is apparent from the results shown in Table 2, Dye (i) has extremely higher storage stability against an alkali agent and maintains excellent dyeing property of the hair even after storage, compared with the methine dyes (ii) to (iv) described in WO99/07334.

TABLE 2

Evaluation of dyeing property

|  | Direct dye | Immediately after preparation | After storage | Remarks |
|---|---|---|---|---|
| Example 2 | Dye (i) | A | A | — |
| Comp. Ex. 4 | Dye (ii) | B | C | Lightening of the color (decomposition of dye) of the dye solution was observed during storage |
| Comp. Ex. 5 | Dye (iii) | B | D |  |
| Comp. Ex. 6 | Dye (iv) | A | D |  |

Examples 3 to 5 and Comparative Examples 7 to 9

Two-part hair dyes as described below were prepared and their storage stability against each of a reducing agent and an alkali agent were evaluated. It should be noted that in each of the hair dyes, the pH of the first component part was 9.5, that of the second component part was 4.3 and that of a mixture thereof was 9.3.

|  | (wt. %) |
|---|---|
| (First component part) |  |
| 25 wt. % Aqueous ammonia | 6.0 |
| Ammonium chloride | 2.7 |
| Ethanol | 10.0 |
| Propylene glycol | 10.0 |

-continued

|  | (wt. %) |
|---|---|
| The dye shown in Table 3 | 0.1 |
| The reducing agent shown in Table 3 | 0.5 |
| Deionized water | balance |
| (Second component part) |  |
| 35 wt. % Aqueous hydrogen peroxide | 17.1 |
| Deionized water | balance |

(Evaluation Method)

In a similar manner and in accordance with similar standards to Example 1 except for the use of each of the above-described hair dyes [first component part:second component part=1:1 (weight ratio)] immediately after preparation and the hair dye 3 months after storage at 40° C., respectively, the dyeing property was evaluated.

(Results)

As is apparent from the results shown in Table 3, Dye (i) has markedly high storage stability against an alkali agent and a reducing agent and maintains excellent dyeing property of the hair even after storage compared with the methine dye (ii) described in WO99/07334.

TABLE 3

|  |  |  | Evaluation of dyeing property |  |  |
|---|---|---|---|---|---|
|  | Direct dye | Reducing agent | Immediately after preparation | After storage | Remarks |
| Ex. |  |  |  |  |  |
| 3 | Dye (i) | Sodium sulfite | A | B | — |
| 4 | Dye (i) | Ammonium thioglycolate | A | A |  |
| 5 | Dye (i) | Ascorbic acid | A | A |  |
| Comp. Ex. |  |  |  |  |  |
| 7 | Dye (ii) | Sodium sulfite | C | D | Lightening of the color (decomposition of dye) of the dye solution was observed during storage |
| 8 | Dye (ii) | Ammonium thioglycolate | C | D |  |
| 9 | Dye (ii) | Ascorbic acid | C | D |  |

Examples 6 to 11 and Comparative Examples 10 to 13

Hair dyes shown in Table 4 (one-part composition) and in Table 5 (two-part composition) were prepared and their stability against each of an alkali agent, oxidizing agent and reducing agent was evaluated.

(Evaluation Methods)

For dyeing, a one-part type hair dye was applied to the hair as a two-part type hair dye in the form of a 1:1 mixture (weight ratio) of the first component part and the second component part.

(1) With regards to the hair dyeing power, 10 g of the above-described composition was applied to a bundle of gray hair (10 g in weight) and the resulting hair bundle was allowed to stand for 20 minutes in a thermostat of 20° C. After rinsing with warm water and washing with shampoo, it was dried. The dyeing property was observed and evaluated based on the below-described standards.

(2) With regards to color fade, the color tone of the hair bundle after repetition of shampooing 20 times was compared with that before treatment and evaluated based on the below-described standards.

(3) With regards to a change in color tone, the color tones of the direct-dye-containing hair dye (the first component part in the case of two-part composition) immediately after preparation and 6 months after storage at 40° C. were compared and evaluated based on the below-described standards.

(Evaluation Standards)

(1) Dyeing Power

A: The hair can be dyed excellently and uniformly.

B: The hair can be dyed well and uniformly.

C: The hair cannot be dyed well.

D: The hair can hardly be dyed.

(2) Color Fading

A: Almost no color fading occurred even after the treatment.

B: A little color fading occurred by the treatment.

C: Much color fading occurred by the treatment.

D: Color fading occurred distinctly by the treatment.

(3) Change in Color Tone

A: Almost no change in the color tone occurred even after treatment.

B: Slight lightening of the color tone occurred by storage.

C: Considerable lightening of the color tone occurred by storage.

D: Lightening of the color tone occurred distinctly by storage.

(Results)

As is apparent from the results shown in Tables 4 and 5, Dye (i) has markedly high stability against any one of an alkali agent, an oxidizing agent and a reducing agent, is markedly superior in the dyeing property of the hair, and can maintain its dyeing property even after storage, compared with the methine dyes (ii) and (iii) described in WO99/07334.

TABLE 4

| | Example | | | Comp Ex. | |
|---|---|---|---|---|---|
| Component (wt. %) | 6 | 7 | 8 | 10 | 11 |
| Dye (i) | 0.5 | 0.3 | 0.3 | — | — |
| Basic Yellow 57 | — | 0.1 | 0.1 | — | — |
| Basic Red 2 | — | — | 0.1 | — | — |
| Dye (ii) | — | — | — | 0.5 | — |
| Dye (iii) | — | — | — | — | 0.5 |
| 28 wt. % Aqueous ammonia | 6 | | | | |
| Ethanol | 15 | | | | |
| Propylene glycol | 10 | | | | |
| Polyoxyethylene (20) octyl dodecyl ether | 10 | | | | |
| Polyoxyethylene (9) tridecyl ether | 3 | | | | |
| Polyoxyethylene (3) tridecyl ether | 6 | | | | |
| Oleic acid diethanolamide | 8 | | | | |
| Oleyl alcohol | 2 | | | | |
| Ammonium chloride | Amount to adjust pH to 9.8 | | | | |
| LPG (4.0 kg · cm) | 10 | | | | |
| Purified water | Balance | | | | |
| Dyeing power | | | | | |
| Dyeing power | A | A | A | B | B |
| Color Fade | A | A | B | B | B |
| Change in color tone | A | A | B | D | D |

TABLE 5

| | Example | | | Comp Ex. | |
|---|---|---|---|---|---|
| Component (wt. %) | 9 | 10 | 11 | 12 | 13 |
| First part | | | | | |
| Dye (i) | 0.5 | 0.3 | 0.3 | — | — |
| Basic Red 2 | — | — | 0.1 | — | — |
| Dye (ii) | — | — | — | 0.5 | — |
| Dye (iii) | — | — | — | — | 0.5 |
| Para-aminophenol | — | 0.2 | — | — | — |
| Toluene-2,5-diamine | — | — | 0.2 | — | — |
| Para-amino-o-cresol | — | 0.2 | 0.2 | — | — |
| 28 wt. % Aqueous ammonia | 6 | 6 | 6 | 6 | 6 |
| Ethanol | 15 | — | — | 15 | 15 |
| Propylene glycol | 10 | 2 | 2 | 10 | 10 |
| Polyoxyethylene (20) octyl dodecyl ether | 10 | — | — | 10 | 10 |
| Polyoxyethylene (40) cetyl ether | — | 2 | 2 | — | — |
| Polyoxyethylene (2) cetyl ether | — | 2.5 | 2.5 | — | — |
| Oleic acid diethanolamide | 8 | — | — | 8 | 8 |
| Oleyl alcohol | 2 | — | — | 2 | 2 |
| Stearyl trimethylammonium chloride | — | 1.5 | 1.5 | — | — |
| Cetanol | — | 1 | 1 | — | — |
| Liquid paraffin | — | 0.5 | 0.5 | — | — |
| Ammonium chloride | Amount to adjust pH to 9.8 | | | | |
| Sodium sulfite | 0.5 | | | | |
| Tetrasodium ethylenediaminetetraacetate | 0.1 | | | | |
| Purified water | Balance | | | | |
| Second part | | | | | |
| 35 wt. % Aqueous hydrogen peroxide | 17.1 | | | | |
| Methylparaben | 0.1 | | | | |
| Phosphoric acid | Amount to adjust pH to 3.5 | | | | |
| Purified water | Balance | | | | |
| Dyeing power | | | | | |
| Dyeing power | A | A | A | C | D |
| Color Fade | A | A | B | A | —*1 |
| Change in color tube | B | B | B | D | D |

*1 not evaluated because the hair was scarcely dyed.

What is claimed is:

1. A hair dye composition comprising, as a direct dye, a compound represented by the following formula (1):

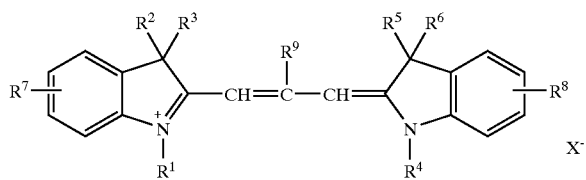

(1)

wherein, $R^1$, $R^2$, $R^3$, $R^4$, $R^5$ and $R^6$ each independently represents a $C_{1-6}$ alkyl group which may have a substituent; $R^7$ and $R^8$ each independently represents a hydroxy group, an amino group which may be substituted with one or two $C_{1-6}$ alkyl groups which may be substituted by a hydroxy group; $R^9$ represents a hydrogen atom or a $C_{1-6}$ alkyl group; and $X^-$ represents an anion.

2. A hair dye composition according to claim 1, comprising, as a direct dye, a compound represented by the following formula (2):

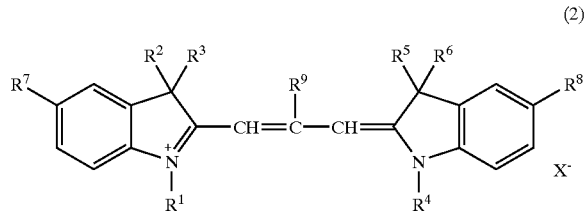

(2)

wherein, $R^1$, $R^2$, $R^3$, $R^4$, $R^5$ and $R^6$ each independently represents a $C_{1-6}$ alkyl group which may have a substituent; $R^7$ and $R^8$ each independently represents a hydroxy group, an amino group which may be substituted with one or two $C_{1-6}$ alkyl groups which may be substituted by a hydroxy group; $R^9$ represents a hydrogen atom or a $C_{1-6}$ alkyl group; and $X^-$ represents an anion.

3. A hair dye composition according to claim 2, $R^7$ and $R^8$ each independently represents a hydroxy group, an amino group or —$NR^{11}$, wherein, $R^{11}$ represents a $C_{1-4}$ alkyl group which may have a substituent.

4. A hair dye composition according to claim 1, which has a pH of 8 or greater.

5. A hair dye composition according to claim 1, which is applied to the hair after mixing with an oxidizing agent.

6. A hair dye composition according to claim 1, further comprising an oxidation dye.

7. A hair dyeing method, which comprises applying to the hair a hair dye composition comprising, as a direct dye, a compound represented by the following formula (1):

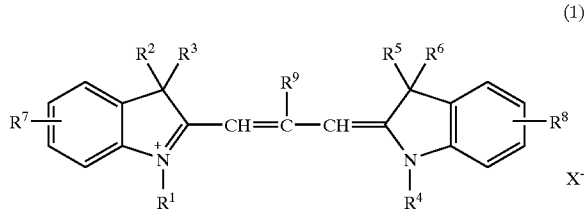

(1)

wherein, $R^1$, $R^2$, $R^3$, $R^4$, $R^5$ and $R^6$ each independently represents a $C_{1-6}$ alkyl group which may have a substituent; $R^7$ and $R^8$ each independently represents a hydroxy group, an amino group which may be substituted with one or two $C_{1-6}$ alkyl groups which may be substituted by a hydroxy group; $R^9$ represents a hydrogen atom or a $C_{1-6}$ alkyl group; and $X^-$ represents an anion.

8. The hair dye composition according to claim 1, wherein said $C_{1-6}$ alkyl group is selected from the group consisting of ethyl, ethyl, propyl, butyl, pentyl, hexyl, isopropyl, isobutyl and isopentyl.

9. The hair dye composition according to claim 1, wherein one or more of $R^1$, $R^2$, $R^3$, $R^4$, $R^5$ and $R^6$ have a substituent selected from the group consisting of a sulfonic acid group, a salt of a sulfonic acid group, a cyano group, a chlorine atom, a hydroxy group, an amino group, an alkoxy group, a monoalkylamino group, a dialkiylamino group, a trimethylammoniumyl group, and an aryl group, or a mixture thereof.

10. The hair dye composition according to claim 1, wherein said amino group which may be substituted with one or two $C_{1-6}$ alkyl groups which may be substituted by a hydroxy group is selected from the group consisting of an amino group, a monomethylamino group, a dimethylamino group, a monoethylamino group, a diethylamino group, a monopropylamino group, a dipropylamino group, mono(2-hydroxyethyl)amino group, a bis(2-hydroxyethyl)amino group, a mono(2-hydroxypropyl)amino group, a bis(2-hydroxypropyl)amino group, a mono(3-hydroxypropyl)amino group, and a bis(3-hydroxypropyl)amino group.

11. The hair dye composition according to claim 1, wherein said anion $X^-$ is selected from the group consisting of chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions, acetic acid ions and perchloric acid ions.

12. The hair dye composition according to claim 1, wherein said compound represented by formula (1) is present at a concentration ranging from 0.01 to 20 wt. % based on the whole composition.

13. The hair dye composition according to claim 1, further comprising at least one additive selected from the group consisting of a direct dye other than the direct dye of formula (1), an alkali agent, an oxidizing agent, a reducing agent, a developer, a coupler, an autoxidation dye, an anionic surfactant, an anionic polymer, a fatty acid, a polyol, a polyol alkyl ether, a cationic polymer, an amphoteric polymer, a silicone, a hydrocarbon, an animal fat, an animal oil, a vegetable fat, a vegetable oil, a higher fatty acid, an organic solvent, a penetration promoter, a cationic surfactant, a natural polymer, a synthetic polymer, a higher alcohol, an ether, an amphoteric surfactant, a nonionic surfactant, a protein derivative, an amino acid, an antiseptic, a chelating agent, a stabilizing agent, an antioxidant, a plant extract, a crude drug extract, a vitamin, a colorant, a perfume, and ultraviolet absorber.

14. The hair dye composition according to claim 1, wherein said hair dye composition is in a form selected from the group consisting of a powder, a transparent liquid, an emulsion, a cream, a gel, a paste, an aerosol, and an aerosol foam.

15. The method according to claim 7, wherein said $C_{1-6}$ alkyl group is selected from the group consisting of ethyl, ethyl, propyl, butyl, pentyl, hexyl, isopropyl, isobutyl and isopentyl.

16. The method according to claim 7, wherein one or more of $R^1$, $R^2$, $R^3$, $R^4$, $R^5$ and $R^6$ have a substituent selected from the group consisting of a sulfonic acid group, a salt of a sulfonic acid group, a cyano group, a chlorine atom, a hydroxy group, an amino group, an alkoxy group, a monoalkylamino group, a dialkiylamino group, a trimethylammoniumyl group, and an aryl group, or a mixture thereof.

17. The method according to claim 7, wherein said amino group which may be substituted with one or two $C_{1-6}$ alkyl groups which may be substituted by a hydroxy group is selected from the group consisting of an amino group, a monomethylamino group, a dimethylamino group, a monoethylamino group, a diethylamino group, a monopropylamino group, a dipropylamino group, mono(2-hydroxyethyl)amino group, a bis(2-hydroxyethyl)amino group, a mono(2-hydroxypropyl)amino group, a bis(2-hydroxypropyl)amino group, a mono(3-hydroxypropyl)amino group, and a bis(3-hydroxypropyl)amino group.

18. The method according to claim 7, wherein said anion $X^-$ is selected from the group consisting of chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions, acetic acid ions and perchloric acid ions.

19. The method according to claim 7, wherein said compound represented by formula (1) is present at a concentration ranging from 0.01 to 20 wt. % based on the whole composition.

20. The method according to claim 7, further comprising at least one additive selected from the group consisting of a direct dye other than the direct dye of formula (1), an alkali agent, an oxidizing agent, a reducing agent, a developer, a coupler, an autoxidation dye, an anionic surfactant, an anionic polymer, a fatty acid, a polyol, a polyol alkyl ether, a cationic polymer, an amphoteric polymer, a silicone, a hydrocarbon, an animal fat, an animal oil, a vegetable fat, a vegetable oil, a higher fatty acid, an organic solvent, a penetration promoter, a cationic surfactant, a natural polymer, a synthetic polymer, a higher alcohol, an ether, an amphoteric surfactant, a nonionic surfactant, a protein derivative, an amino acid, an antiseptic, a chelating agent, a stabilizing agent, an antioxidant, a plant extract, a crude drug extract, a vitamin, a colorant, a perfume, and ultraviolet absorber.

21. The method according to claim 7, wherein said hair dye composition is in a form selected from the group consisting of a powder, a transparent liquid, an emulsion, a cream, a gel, a paste, an aerosol, and an aerosol foam.

* * * * *

UNITED STATES PATENT AND TRADEMARK OFFICE
CERTIFICATE OF CORRECTION

| | | |
|---|---|---|
| PATENT NO. | : 6,878,169 B2 | Page 1 of 1 |
| APPLICATION NO. | : 10/319589 | |
| DATED | : April 12, 2005 | |
| INVENTOR(S) | : Kenichi Matsunaga | |

It is certified that error appears in the above-identified patent and that said Letters Patent is hereby corrected as shown below:

Column 14, line 3, "ethyl, ethyl" should read --methyl, ethyl-- line 10, "dialkiylamino" should read --dialkylamino-- line 56, "consisting of ethyl" should read --consisting of methyl-- line 64, "dialkiylamino" should read --dialkylamino--

Signed and Sealed this

Twenty-eighth Day of August, 2007

JON W. DUDAS
*Director of the United States Patent and Trademark Office*